(12) United States Patent
Yoshimura et al.

(10) Patent No.: US 8,926,996 B2
(45) Date of Patent: Jan. 6, 2015

(54) OIL-IN-WATER COSMETICS

(75) Inventors: Masanori Yoshimura, Yokohama (JP);
Yuji Matsushita, Yokohama (JP);
Takafumi Kurosawa, Yokohama (JP)

(73) Assignee: Shiseido Company, Ltd., Tokyo (JP)

( * ) Notice: Subject to any disclaimer, the term of this patent is extended or adjusted under 35 U.S.C. 154(b) by 226 days.

(21) Appl. No.: 13/132,112

(22) PCT Filed: Dec. 3, 2009

(86) PCT No.: PCT/JP2009/070298
§ 371 (c)(1),
(2), (4) Date: Jun. 1, 2011

(87) PCT Pub. No.: WO2010/064678
PCT Pub. Date: Jun. 10, 2010

(65) Prior Publication Data
US 2011/0236447 A1   Sep. 29, 2011

(30) Foreign Application Priority Data
Dec. 3, 2008 (JP) ................. 2008-308876

(51) Int. Cl.
A61K 8/02   (2006.01)
A61K 8/06   (2006.01)
A61K 8/34   (2006.01)
A61K 8/39   (2006.01)
A61K 8/86   (2006.01)
A61Q 17/04  (2006.01)

(52) U.S. Cl.
CPC . *A61K 8/06* (2013.01); *A61K 8/062* (2013.01); *A61K 8/34* (2013.01); *A61K 8/39* (2013.01); *A61K 8/86* (2013.01); *A61Q 17/04* (2013.01)
USPC ............ 424/401; 424/59; 424/60; 424/78.03; 514/547

(58) Field of Classification Search
CPC ........... A61K 8/06; A61K 8/062; A61K 8/34; A61K 8/39; A61K 8/86; A61Q 17/04
See application file for complete search history.

(56) References Cited

U.S. PATENT DOCUMENTS

| | | |
|---|---|---|
| 4,670,185 A | 6/1987 | Fujiwara et al. |
| 5,693,255 A | 12/1997 | Okamoto et al. |
| 5,902,569 A | 5/1999 | Oshima et al. |
| 6,150,425 A | 11/2000 | Sekine et al. |
| 6,299,887 B1 | 10/2001 | Yano et al. |
| 2007/0261293 A1 | 11/2007 | Tajima et al. |
| 2011/0002873 A1 | 1/2011 | Omura et al. |

FOREIGN PATENT DOCUMENTS

| | | |
|---|---|---|
| EP | 2221046 A1 | 8/2010 |
| JP | 4-005213 | 1/1992 |
| JP | 6-271421 | 9/1994 |
| JP | 8-175953 | 7/1996 |
| JP | 9-301847 | 11/1997 |
| JP | 11-76798 | 3/1999 |
| JP | 2005-206555 | 8/2005 |
| JP | 2006-056861 | 3/2006 |
| JP | 2006-347955 | 12/2006 |
| JP | 3855203 B2 | 12/2006 |
| JP | 2007-063183 | 3/2007 |
| JP | 2007-077178 A | 3/2007 |
| JP | 2007-238516 | 9/2007 |
| JP | 2008-055250 A | 3/2008 |
| JP | 4178397 B2 | 11/2008 |
| JP | 2009-102236 | 5/2009 |
| RU | 2331464 C1 | 8/2008 |

OTHER PUBLICATIONS

English Abstract of JP 2006239666 A (Corresponds to JP 3855203 B2, published Dec. 6, 2006, Applicant—Univ. Kanagawa), 1 Page.
English Abstract of JP 2008-055250 A. Published Mar. 13. 2008, Applicant—Univ. Kanagawa, 1 Page.
English Abstract of JP 2007-077178 A, Published Mar. 29, 2007, Applicant—Univ. Kanagawa, 1 Page.
English Abstract of JP 4178397 B2, Published Nov. 2, 2008. Applicant—Univ. Kanagawa, 1 Page.

(Continued)

*Primary Examiner* — Lezah Roberts
*Assistant Examiner* — Nannette Holloman
(74) *Attorney, Agent, or Firm* — Rankin, Hill & Clark LLP

(57) ABSTRACT

The present invention provides an oil-in-water cosmetic excellent in emulsion stability. The oil-in-water cosmetic includes (a) oil-droplet particles consisting of an oil component to be emulsified; (b) vesicle particles for stabilizing the oil-droplet particles; and (c) an aqueous phase containing water and a monohydric aliphatic alcohol having 1 to 4 carbon atoms. It is preferred that the vesicle particles are formed with an amphiphilic substance which spontaneously forms vesicle particles, and that they are localized on surfaces of the oil-droplet particles. It is preferred that the amphiphilic substance be a polyoxyethylene hydrogenated castor oil derivative represented by the following formula (I), wherein E=L+M+N+X+Y+Z, and that said E which represents the average addition mole number of ethylene oxide is 10 to 20.

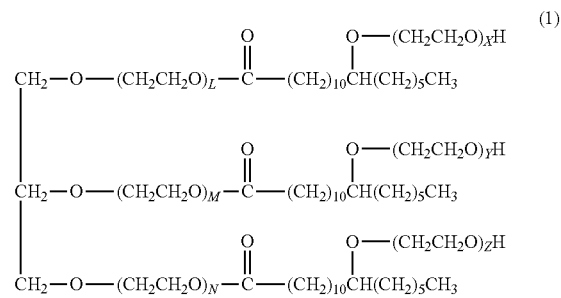

10 Claims, 5 Drawing Sheets

(56) References Cited

OTHER PUBLICATIONS

Espacenet Bibliographic Data for JP 6271421 published Sep. 27, 1994, one page.
Horiuchi et al., "Thermal Properties of Aqueous Vesicle Dispersion Formed with Poly(oxyethylene) hydrogenated Cstor Oil," Journal of the Japan Oil Chemists' Society, 1992, col. 41, No. 12, pp. 1197 to 1202.
Espacenet Bibliographic Data for JP 4005213 published Jan. 9, 1992, one page.
Espacenet Bibliographic Data for JP 8175953 published Jul. 9, 1996, one page.
Espacenet Bibliographic Data for JP 2007238516 published Sep. 20, 2007, one page.
Espacenet Bibliographic Data for JP 11076798 published Mar. 23, 1999, one page.
Espacenet Bibliographic Data for JP 2009102236 published May 14, 2009, one page.
Espacenet Bibliographic Data for JP 9301847 published Nov. 25, 1997, one page.
Patent Abstracts of Japan, Publication No. 2007-063183, seven pages, Mar. 15, 2007.
Patent Abstracts of Japan, Publication No. 2006-056861, forty pages, Mar. 2, 2006.
Patent Abstracts of Japan, Publication No. 2006-347955, eleven pages, Dec. 28, 2006.
Patent Abstracts of Japan, Publication No. 2005-206555, eleven pages, Aug. 4, 2005.
Extended European Search Report, Application No. 09830444, dated May 22, 2012, ten pages.

(a)

(b)

OIL-IN-WATER COSMETICS

RELATED APPLICATIONS

This application claims the priority of Japanese Patent Application No. 2008-308876 filed on Dec. 3, 2008, which is incorporated herein by reference.

FIELD OF THE INVENTION

The present invention relates to an oil-in-water cosmetic, particularly improvement of emulsion stability of an oil-in-water cosmetic containing a lower alcohol.

BACKGROUND OF THE INVENTION

Generally, when an oil-in-water emulsification is conducted using oils including functional oils, an emulsification method wherein a lipophilic surfactant and a hydrophilic surfactant are used in combination so as to meet with the HLB required for materials to be emulsified has been applied. However, such a method requires highly-complicated and great effort to select surfactants optimum for the emulsification. Moreover, when various kinds of oils are present in combination, or when the blending ratio of oils such as silicone oil and polar oil is large, the emulsion stability is poor. Thus, it has been difficult to obtain an oil-in-water cosmetic with a good stability.

In contrast, it has already been reported that, the three-phase emulsification method wherein emulsification is carried out by adhering vesicle particles of an amphiphilic substance, which is present as an independent phase in an oil/amphiphilic substance/water system, to the surface of an oily base due to van der Waals' force provides much higher stability compared with conventional O/W emulsions (Patent Literature 1).

However, even in such a three-phase emulsification method, the emulsion stability was not satisfactory.

On the other hand, a lower alcohol is used by preference in various cosmetics because it provides the skin with a pleasant cooling sensation and a quick-drying feeling, and also it has astringent, cleansing, antiseptic properties as well as promoting effect on drying. When a large amount of lower alcohol is contained in an emulsified composition such as a milky lotion and a cream, a light feeling in use can be provided: however, hardness or viscosity of the system was generally lowered and the emulsion stability tended to become poor.

PRIOR ART DOCUMENTS

Patent Literature

Patent Literature 1: Japanese Patent No. 3855203

DISCLOSURE OF THE INVENTION

Problem to be Solved by the Invention

The present invention was made in view of the above-mentioned conventional problems, and the object is to provide an oil-in-water cosmetic with a good emulsion stability.

Means to Solve the Problem

The present inventors have diligently studied to accomplish the object. As a result, they have found that, contrary to the conventional recognition, the emulsion stability is improved when a lower alcohol is used in the three-phase emulsified oil-in-water composition as mentioned above. For example, the oil-in-water cosmetic with a good emulsion stability can be obtained by mixing an aqueous phase containing a lower alcohol and an amphiphilic substance which spontaneously forms vesicles to prepare vesicle dispersion in which vesicle particles are formed in the aqueous phase, and then mixing an oil component to be emulsified with the dispersion. In the above-mentioned Patent Literature 1, there is no description about a cosmetic containing a lower alcohol and no description that the emulsion stability would be improved by a lower alcohol.

The first aspect of the present invention is an oil-in-water cosmetic comprising:
(a) oil-droplet particles consisting of an oil component to be emulsified;
(b) vesicle particles for stabilizing the oil-droplet particles; and
(c) an aqueous phase containing water and a monohydric aliphatic alcohol having 1 to 4 carbon atoms.

In the oil-in-water cosmetic, it is preferred that the vesicle particles are formed of an amphiphilic substance which spontaneously forms vesicle particles, and the vesicle particles are localized on surfaces of the oil-droplet particles.

In the oil-in-water cosmetic, it is preferred that the amphiphilic substance is a polyoxyethylene hydrogenated castor oil derivative represented by the following formula (1) and the E which represents the average addition mole number of ethylene oxide is 10 to 20.

$$\begin{aligned}
&CH_2\text{—}O\text{—}(CH_2CH_2O)_L\text{—}\overset{O}{\overset{\|}{C}}\text{—}(CH_2)_{10}\overset{O\text{—}(CH_2CH_2O)_XH}{\overset{|}{C}H}(CH_2)_5CH_3 \\
&CH_2\text{—}O\text{—}(CH_2CH_2O)_M\text{—}\overset{O}{\overset{\|}{C}}\text{—}(CH_2)_{10}\overset{O\text{—}(CH_2CH_2O)_YH}{\overset{|}{C}H}(CH_2)_5CH_3 \\
&CH_2\text{—}O\text{—}(CH_2CH_2O)_N\text{—}\overset{O}{\overset{\|}{C}}\text{—}(CH_2)_{10}\overset{O\text{—}(CH_2CH_2O)_ZH}{\overset{|}{C}H}(CH_2)_5CH_3
\end{aligned} \quad (1)$$

In the formula (I), $E=L+M+N+X+Y+Z$.

In any of the oil-in-water cosmetics, the alcohol contained therein is 5 to 50% by mass with respect to total amount of cosmetic.

In any of the oil-in-water cosmetics, it is preferable that the cosmetic comprises an UV absorber. In the oil-in-water cosmetic, the UV absorber is preferably one or more selected from octocrylene, octyl methoxycinnamate, 4-tert-butyl-4'-methoxybenzoylmethane, methylene bis-benzotriazolyl tetramethylbutylphenol, bis-ethylhexyloxyphenol methoxyphenyl triazone, diethylamino hydroxybenzoyl hexyl benzoate, ethylhexyl triazone, phenylbenzimidazole sulfonic acid, dimethicone diethylbenzalmalonate, diethylhexyl butamido triazone, and 2-(4-(2-ethylhexyloxy)-2-hydroxyphenyl)-2H-benzotriazol.

In any of the oil-in-water cosmetics, it is preferable that the cosmetic further comprises one or more selected from carboxyvinyl polymer, succinoglycan, agar, hydroxyethyl cellulose, hydroxypropyl cellulose, and xanthan gum.

A second aspect of the present invention is a production method of an oil-in-water cosmetic, comprising:
mixing an aqueous phase comprising water and a monohydric aliphatic lower alcohol having 1 to 4 carbon atoms with an amphiphilic substance which spontaneously forms vesicles to prepare a vesicle dispersion in which vesicle particles are formed in the aqueous phase; and mixing an oil component to be emulsified with the vesicle dispersion to obtain the oil-in-water cosmetic.

Effect of the Invention

According to the present invention, with use of a lower alcohol, it is possible to significantly improve the stability of the oil-in-water cosmetic wherein oil-droplet particles are emulsified in the aqueous phase by adhering vesicle particles to the oil-droplet particles consisting of an oil component to be emulsified.

BEST MODE FOR CARRYING OUT THE INVENTION

Figure 1:
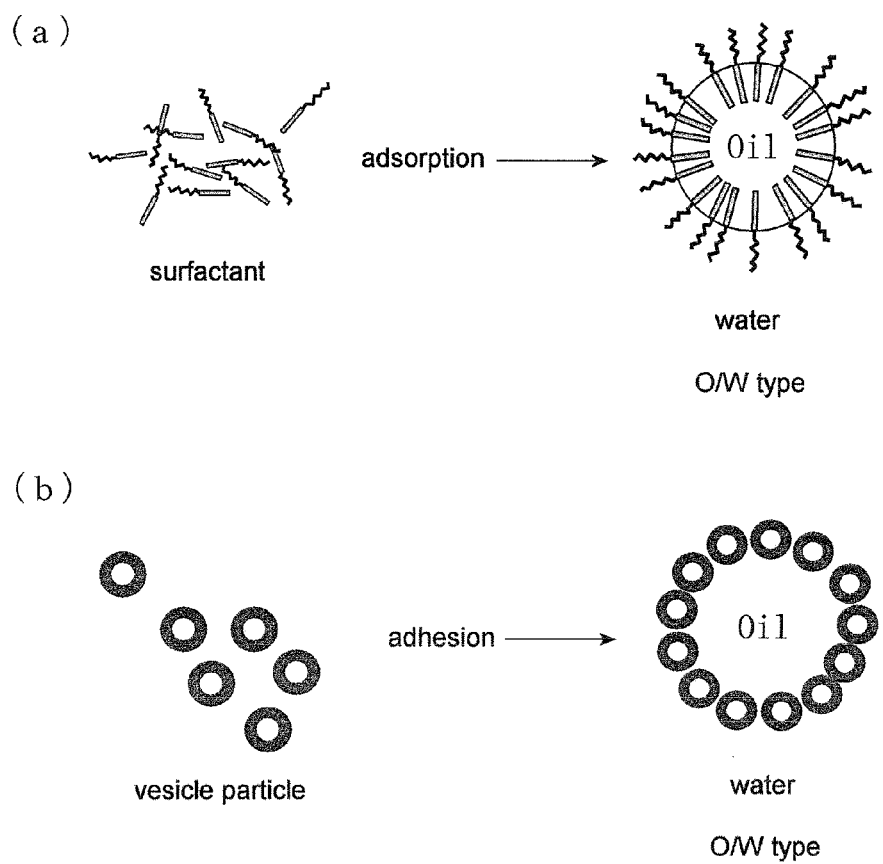
FIG. 1 includes diagrams showing the mechanism of emulsification, (a) is a diagram illustrating a monomolecular-film adsorption mechanism of a conventional surfactant, and (b) is a diagram illustrating an adhesion mechanism of vesicle particles.

Hereinafter, the embodiments of the present invention will be explained in details. However, the present invention is not limited thereto.

The oil-in-water cosmetic of the present invention is a three-phase emulsified oil-in-water composition in which an oil component to be emulsified is emulsified and dispersed as oil-droplet particles in an aqueous phase and vesicle particles are localized on the surfaces of the oil-droplet particles. Therefore, the emulsion stability of the oil-in-water cosmetic is superior to those of conventional oil-in-water compositions. Furthermore, with use of a lower alcohol, the emulsion stability of the oil-in-water composition is superior to even those of conventional three-phase emulsified oil-in-water compositions.

The oil-in-water cosmetic of the present invention can be preferably obtained by adding an amphiphilic substance which spontaneously forms vesicle particles to an aqueous phase containing water and a lower alcohol, mixing them with use of a stirrer such as a homomixer to prepare a vesicle dispersion in which vesicle particles are formed in the aqueous phase, mixing an oil component to be emulsified with the obtained dispersion to carry out emulsification. The lower alcohol has only to coexist with vesicle particles at least prior to the emulsification. For example, it is possible to add the lower alcohol after vesicles are formed in the aqueous phase containing no lower alcohol, and then mix and emulsify the oil component to be emulsified therewith. In terms of stabilization effect, it is more preferred that, as mentioned above, vesicles be formed in the aqueous phase to which a lower alcohol has been added in advance.

To the aqueous phase used in the present invention, aqueous components other than water and a lower alcohol can be added. These aqueous components are not limited in particular, and in addition to aqueous solvents, those generally used in cosmetics, pharmaceuticals, and so on may be incorporated in the range that the stability is not affected.

The amount of aqueous phase is not limited in particular and generally 20 to 90% by mass in the cosmetic.

The lower alcohol used in the present invention can be a monohydric aliphatic alcohol having 1 to 4 carbon atoms. The examples include one or more alcohols such as ethanol, methanol, propanol, isopropanol, butanol, and isobutanol. Particularly, ethanol is preferably used considering stability.

The amount of lower alcohol used in the present invention is not limited in particular and preferably 5 to 50% by mass with respect to the total amount of cosmetic. When the amount of lower alcohol is too small, a sufficient emulsion stabilization effect may not be achieved. Though the emulsion stabilization effect is enhanced as the amount of lower alcohol is increased, the emulsion stability is not further enhanced after the amount exceeds 50% by mass: thus using such a large amount of lower alcohol is uneconomical. In addition, a large amount of lower alcohol may provide a poor feeling in use.

As the oil component to be emulsified, any oil components can be used so far as they are generally used in cosmetics. For example, any components selected from components such as oils and fats, waxes, hydrocarbon oils, silicone oils, higher fatty acids, higher alcohols, synthetic ester oils, and natural ester oils can be incorporated, and they are not limited in particular so far as they don't deteriorate the effect of the present invention.

The amount of the oil component to be emulsified is not limited in particular, and the total amount is generally 0.1 to 30% by mass in the cosmetic.

Examples of oils and fats include avocado oil, camellia oil, turtle oil, macadamia nut oil, corn oil, mink oil, olive oil, rapeseed oil, egg oil, sesame oil, persic oil, wheat germ oil, sasanqua oil, castor oil, linseed oil, safflower oil, cottonseed oil, perilla oil, soybean oil, peanut oil, tea seed oil, kaya oil, rice bran oil, paulownia oil, Japanese tung oil, jojoba oil, germ oil, triglycerin, cacao butter, coconut oil, horse fat, hardened coconut oil, palm oil, beef tallow, mutton tallow, hardened beef tallow, palm kernel oil, pork tallow, beef bone tallow, Japan wax kernel oil, hardened oil, heatsfoot oil, Japan wax, and hardened castor oil.

Examples of waxes include beeswax, candelilla wax, cotton wax, carnauba wax, bayberry wax, Chinese wax, spermaceti wax, montan wax, rice bran wax, lanolin, kapok wax, lanolin acetate, liquid lanolin, sugar cane wax, isopropyl lanolate, hexyl laurate, reduced lanolin, jojoba wax, hard lanolin, shellac wax, POE lanoline alcohol ether, POE lanoline alcohol acetate, POE cholesterol ether, lanolin fatty acid polyethylene glycol ester, and POE hydrogenated lanolin alcohol ether.

Examples of hydrocarbon oils include isohexadecane and isododecane.

Examples of silicone oils include linear and cyclic polysiloxanes such as dimethylpolysiloxane, methylphenylpolysiloxane, methylhydrogenpolysiloxane, decamethylpolysiloxane, dodecamethylpolysiloxane, tetramethyltetrahydrogenpolysiloxane, cyclotetradimethylsiloxane, and cyclopentadimethylsiloxane.

Examples of higher fatty acids include lauric acid, myristic acid, palmitic acid, stearic acid, behenic acid, oleic acid, undecylenic acid, tallic acid, isostearic acid, linoleic acid, linolenic acid, eicosapentaenoic acid (EPA), and docosahexaenoic acid (DHA).

Examples of higher alcohols include linear alcohols such as lauryl alcohol, cetyl alcohol, stearyl alcohol, behenyl alcohol, myristyl alcohol, oleyl alcohol, and cetostearyl alcohol; and branched-chain alcohols such as monostearyl glycerin ether (batylalcohol), 2-decyltetradecynol, lanolin alcohol, cholesterol, phytosterol, hexyldodecanol, isostearyl alcohol, and octyldodecanol.

Examples of synthetic ester oils include isopropyl myristate, cetyl octanoate, octyldodecyl myristate, isopropyl palmitate, butyl stearate, hexyl laurate, myristyl myristate, decyl oleate, hexyldecyl dimethyloctanoate, cetyl lactate, myristyl lactate, lanolin acetate, isocetyl stearate, isocetyl isostearate, cholesteryl 12-hydroxystearate, ethylene glycol di-2-ethylhexanoate, dipentaerythritol fatty acid ester, N-alkyl glycol monoisostearate, neopentylglycol dicaprate, diisostearyl malate, glyceryl di-2-heptylundecanoate, trimethylolpropane tri-2-ethylhexanoate, trimethylolpropane triisostearate, pentanerythritol tetra-2-ethylhexanoate, glyceryl tri-2-ethylhexanoate, cetyl 2-ethylhexanoate, 2-ethylhexyl palmitate, glyceryl trimyristate, glyceryl tri-2-heptylundecanoate, castor oil fatty acid methyl ester, oleyl oleate, cetostearyl alcohol, acetoglyceride, 2-heptylundecyl palmitate, diisobutyl adipate, 2-octyldodecyl N-lauroyl-L-glutamate, di-2-heptylundecyl adipate, ethyl laurate, di-2-ethylhexyl sebacate, 2-hexyldecyl myristate, 2-hexyldecyl palmitate, 2-hexyldecyl adipate, diisopropyl sebacate, 2-ethylhexyl succinate, ethyl acetate, butyl acetate, amyl acetate, and triethyl citrate.

Examples of natural ester oils include avocado oil, camellia oil, turtle oil, macadamia nut oil, corn oil, mink oil, olive oil, rapeseed oil, egg oil, sesame oil, persic oil, wheat germ oil, sasanqua oil, castor oil, linseed oil, safflower oil, cottonseed oil, perilla oil, soybean oil, peanut oil, tea seed oil, kaya oil, rice bran oil, paulownia oil, jojoba oil, germ oil, triglycerin, glyceryl trioctanoate, and glyceryl triisopalmitate.

When an ester oil is used, the IOB value is preferably 0.1 to 0.6. When an ester oil with IOB value of less than 0.1 is used, a light feeling in use is not provided, and a sticky touch may be caused. On the other hand, when an ester oil with IOB value of more than 0.6 is used, it easily dissolves in water and no longer functions as an oil component, which may result in a poor emulsion stability.

The organic conception diagram theory specifying the IOB value will be explained here. In the organic conception diagram, assuming that the origin of all organic compounds is methane ($CH_4$) and that other compounds are methane derivatives, a specific numerical value is set for each of carbon atom number, substituent, modified portion, ring, and so on, to calculate the organic and inorganic values from the sum of scores. Then, the organic value and the inorganic value were respectively marked on the X and Y axes of a diagram. This organic conception diagram is described in "Yuuki Gainen Zu—Kiso To Ohyoh—" (Organic Conception Diagram—Fundamentals and Applications—), Yoshio KODA, Sankyo Shuppan, (1984), etc. The IOB value in the organic conception diagram means the ratio of inorganic value (IV) with respect to organic value (OV), that is, "inorganic value (IV)/organic value (OV)".

The ester oil with IOB value of 0.1 to 0.6 is not limited in particular, and the examples include: isopropyl myristate (IOB=0.18), isodecyl isononanoate (IOB=0.19), octyldodecyl neopentanoate (IOB=0.13), isostearyl neopentanoate (IOB=0.14), isopropyl palmitate (IOB=0.16), hexyl laurate (IOB=0.17), hexyldecyl ethylhexanoate (IOB=0.13), isotridecyl isononanoate (IOB=0.16), isopropyl isostearate (IOB=0.15), ethyl isostearate (IOB=0.15), ethylhexyl palmitate (IOB=0.13), octyldodecyl neodecanoate (IOB=0.11), polyglyceryl-2 tetraisostearate (IOB=0.17), pentaerythrityl tetraisostearate (IOB=0.15), isocetyl myristate (IOB=0.10), trimethylolpropane triisostearate (IOB=0.16), neopentyl glycol diethylhexanoate (IOB=0.32), trimethylolpropane triethylhexanoate (IOB=0.33), pentaerythrityl tetraethylhexanoate (IOB=0.35), diisopropyl adipate (IOB=0.46), diisostearyl malate (IOB=0.28), neopentyl glycol dicaprate (IOB=0.25), tripropylene glycol dineopentanoate (IOB=0.52), isodecyl benzoate (IOB=0.23), propylene glycol dicaprate (IOB=0.32), isononyl isononate (IOB=0.2), ethylhexyl isononate (IOB=0.2), isodecyl neopentanoate (IOB=0.22), ethylhexyl ethylhexanoate (IOB=0.2), cetyl ethylhexanoate (IOB=0.13), glyceryl triethylhexanoate (IOB=0.36), and diethylhexyl succinate (IOB=0.32).

Also, so-called "hydrating oil", which has excellent solubility in water and can absorb (retain) a large amount of water, can be incorporated as an oil component. A hydrating oil contributes to moisturizing property and/or emollient property, has no sticky feeling, and even provides a fresh feeling owing to water retention.

A hydrating oil is an oil having water retention ability. In particular, an oil having water-retaining power of 100% or higher, i.e., an oil that can retain water of the self weight or more is preferably used.

Examples of such hydrating oils include esters such as propylene glycol monoalkyl ester, dipropylene glycol monoalkyl ester, trimethylolpropane dialkyl ester, erythritol trialkyl ester, and tetraglycerin pentaalkyl ester. Specific examples include amino-acid ester oils such as dioctyldodecyl lauroyl glutamate, di(cholesteryl/behenyl/octyldodecyl) N-lauroyl-L-glutamate, di(phytosteryl/behenyl/octyldodecyl) N-lauroyl-L-glutamate, and di(phytosteryl/2-octyldodecyl) N-lauroyl-L-glutamate; pentaerythritol benzoic acid ester oils such as pentaerythritol tetra(behenate/benzoate/ethylhexanoate); glycerin fatty acid ester oils such as glyceryl diisostearate and triethylhexanoin; carbonic acid ester oils such as diethylhexyl succinate, diisopropyl sebacate, and tripropylene glycol pivalate; polyhydric alcohol fatty acid esters such as caster oil and shea butter; hexaglycerin fatty acid esters; decaglycerin fatty acid esters; glyceryl ethylhexanoate/stearate/adipate; and dipentaerythritol fatty acid esters such as dipentaerythritol (12-hydroxystearate/stearate/rosinate), and dipentaerythritol (12-hydroxystearate/isostearate).

Examples of other hydrating oils include cholesterol derivatives such as cholesterol, cholestanol, dehydrocholesterol, cholesteryl lanolate, cholesteryl isostearate, cholesteryl hydroxystearate, cholesteryl ricinoleate, and cholesteryl macadamiate; phytosterol derivatives; lanolin derivatives such as lanolin, adsorption purified lanolin, liquid lanolin, reduced lanolin, lanolin acetate, lanolin alcohol, hydrogenated lanolin alcohol, and lanolin fatty acid; and polyoxyalkylene-modified derivatives thereof.

In particular, it is preferred that one or more selected from amino acid esters, pentaerythritol benzoic acid esters, glycerin fatty acid esters, and carbonic acid esters be incorporated as the hydrating oil. Furthermore, among the above-mentioned hydrating oils, it is more preferred that one or more selected from pentaerythritol tetra(behenate/benzoate/ethylhexanoate), glyceryl diisostearate, and di(phytosteryl/2-octyldodecyl) N-lauroyl-L-glutamate be incorporated.

The nature of hydrating oil is not limited in particular, and the hydrating oil which is liquid at ordinary temperature (e.g., glyceryl diisostearate) or the one which is semi-solid at ordinary temperature (e.g., di(phytosteryl/2-octyldodecyl) N-lauroyl-L-glutamate) can be incorporated. Also, hydrating oils having different nature from each other can be used in combination.

Examples of amphiphilic substance which forms vesicles of the present invention include derivatives of polyoxyethylene hydrogenated castor oil; halide salts of dialkyl ammonium derivatives, trialkyl ammonium derivatives, tetraalkyl ammonium derivatives, dialkenyl ammonium derivatives, trialkenyl ammonium derivatives, and tetraalkenyl ammonium derivatives; phospholipids; and phospholipid derivatives. Among them, derivatives of polyoxyethylene hydrogenated castor oil represented by the following formula (1) are more preferably used.

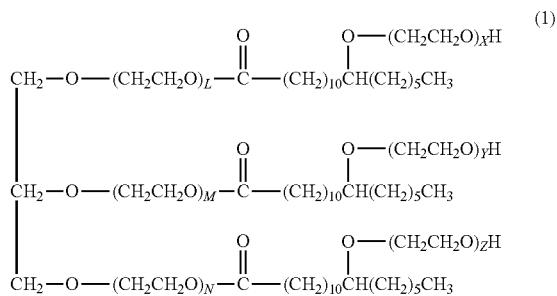

In the formula (I), $E=L+M+N+X+Y+Z$.

As the polyoxyethylene hydrogenated castor oil derivative, the derivative having the average addition mole number (E) of ethylene oxide (EO) of 10 to 20 can be used. When the average addition mole number of EO is less than 10, vesicle particles are not spontaneously formed in the aqueous phase, thus the oil-in-water cosmetic of the present invention cannot be obtained. When it exceeds 20, sufficient emulsion stability cannot be achieved, and a slimy touch is felt: thus, a product with satisfactory stability and usability cannot be obtained.

Also, two or more of the above-mentioned polyoxyethylene hydrogenated castor oil derivatives can be used in combination.

The amount of amphiphilic substance is not limited in particular, and the total amount is generally 0.1 to 10% by mass in the cosmetic.

In the present invention, one or more of thickeners which can be generally contained in cosmetics can be incorporated. Though the thickeners may be present in the aqueous phase when vesicles are formed, they may be added after emulsification. By incorporating thickeners, the viscosity of cosmetic is increased to enhance the usability, and also, the emulsion stability over time is further improved. The total amount of thickeners is preferably 0.1 to 3% by mass with respect to the total amount of cosmetic. The above-mentioned effect is not sufficient when the amount is too small, and deterioration in usability such as lumps may be caused when the amount is too large.

Examples of thickeners include natural and synthetic water-soluble polymers, and specifically plant-derived polymers such as gum arabic, tragacanth, galactan, carob gum, guar gum, karaya gum, carrageenan, pectin, quince seed (quince), starch (rice, corn, potato, and wheat), algae colloid (brown algae extract), and agar; microorganism-derived polymers such as dextran, succinoglycan, and pullulan; animal-derived polymers such as collagen, casein, albumin, and gelatin; starch-based polymers such as carboxymethyl starch and methylhydroxypropyl starch; cellulose-based polymers such as methyl cellulose, nitrocellulose, ethyl cellulose, methylhydroxypropyl cellulose, hydroxyethyl cellulose, sodium cellulose sulfate, hydroxypropyl cellulose, sodium carboxymethyl cellulose, crystalline cellulose, and cellulose powder; alginic acid-based polymers such as sodium alginate and propylene glycol alginate; vinyl-based polymers such as polyvinyl methyl ether, carboxyvinyl polymer (e.g., CARBOPOL), and alkyl-modified carboxyvinyl polymer (e.g., PEMULEN); polyoxyethylene polymers; polyoxyethylene polyoxypropylene copolymers; acryl polymers such as sodium polyacrylate, polyethyl acrylate, and polyacrylamide; polyethyleneimine; cationic polymers; and inorganic water-soluble polymers such as bentonite, magnesium aluminium silicate, laponite, hectorite, and silicic anhydride.

Among them, preferred examples of thickeners include carboxyvinyl polymer, succinoglycan, agar, hydroxyethyl cellulose, hydroxypropyl cellulose, and xanthan gum.

Also, an acrylamide thickener can be preferably incorporated. It contributes to emulsion stability as well as can provide elasticity with the skin.

Examples of acrylamide thickeners include homopolymers, copolymers, cross-polymers, or mixtures thereof, which contain, as a constitutional unit, one or more selected from 2-acrylamido-2-methylpropanesulfonic acid (AMPS), acrylic acid, and derivatives thereof. The specific examples include vinylpyrrolidone/AMPS copolymer, dimethylacrylamide/AMPS copolymer, acrylamide/AMPS copolymer, dimethylacrylamide/AMPS cross-polymer which is cross-linked with methylene-bis-acrylamide, a mixture of polyacrylamide and sodium polyacrylate, sodium acrylate/AMPS copolymer, hydroxyethyl acrylate/AMPS copolymer, acrylamide/ammonium acrylate copolymer, and acrylamide/sodium acrylate copolymer. Among them, preferred examples include homopolymers of AMPS, vinylpyrrolidone/AMPS copolymer, dimethylacrylamide/AMPS copolymer, sodium acrylate/AMPS copolymer, and dimethylacrylamide/AMPS cross-polymer which is cross-linked with methylene-bis-acrylamide. One or more of the above-mentioned acrylamide thickeners can be incorporated.

Succinoglycan, xanthan gum, and acrylamide thickeners have salt resistance. Among them, succinoglycan has strong retention power under temperature change and shows high yield value. Also, it has excellent effect in usability such as fresh feeling in use.

Succinoglycan is a kind of microbially-derived polysaccharides. Specifically, succinoglycan means a microbially-derived polysaccharide which contains, in addition to the sugar units derived from galactose and glucose, units derived from a succinic acid, a pyruvic acid, and optionally an acetic acid, or salts of these acids.

More specifically, succinoglycan is a water-soluble polymer, wherein galactose unit:glucose unit:succinic acid unit:pyruvic acid unit is 1:7:0.8:1, and acetic acid unit may be optionally contained, with the average molecular weight of about 6,000,000, represented by the following structural formula.

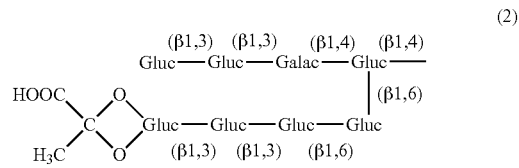

In the formula (2), Gluc represents a glucose unit, and Galac represents a galactose unit. The representations in the parentheses indicate binding patterns between the sugar units. For example, (β1,4) indicates β1-4 binding.

Examples of microbes which are sources of this succinoglycan include bacteria belonging to *Pseudomonas, Rhizobium, Alcaligenes*, or *Agrobacterium*. Among these bacteria,

*Agrobacterium tumefaciens* I-736 (deposited on Mar. 1, 1988 to the Collection Nationale de Cultures de Microorganismes (CNCM) under the Budapest Treaty, publicly-obtainable using accession No. I-736), which belongs to *Agrobacterium*, is particularly preferable as the source of succinoglycan.

Succinoglycan can be produced by culturing these microbes in a medium. More specifically, succinoglycan is generally produced by culturing the above-descried microbes in the medium containing carbon sources such as glucose, sucrose, and hydrolysis products of starch; organic nitrogen sources such as casein, caseinate, vegetable powder, yeast extract, and corn steep liquor (CSL); inorganic salts such as metal sulfates, metal phosphates, and metal carbonates; and optional trace elements.

Not only can succinoglycan, as it is, be incorporated in the oil-in-water cosmetic, but also the degradation products by acid decomposition, alkaline decomposition, enzymatic decomposition, and ultrasonic treatment can be incorporated as necessary.

Also, the oil-in-water cosmetic of the present invention can be preferably used in sunscreen cosmetics by incorporating UV absorbers or UV protection agents.

Any UV absorbers generally used in cosmetics can be preferably used. The examples include benzoic acid derivative UV absorbers such as p-aminobenzoic acids; anthranilic acid derivative UV absorbers such as methyl anthranilate; salicylic acid derivative UV absorbers such as octyl salicylate, phenyl salicylate, and homomenthyl salicylate; dibenzoylmethane derivative UV absorbers; benzophenone derivative UV absorbers such as 2,4-dihydroxybenzophenone, 2,2'-dihydroxy-4-methoxybenzophenone, 2,2'-dihydroxy-4,4'-dimethoxybenzophenone, 2,2',4,4'-tetrahydroxybenzophenone, 2-hydroxy-4-methoxybenzophenone, 2-hydroxy-4-methoxy-4'-methylbenzophenone, 2-hydroxy-4-methoxybenzophenone-5-sulfonic acid, and sodium 2-hydroxy-4-methoxybenzophenone-5-sulfonate; diphenylacrylate derivative UV absorbers such as octocrylene; benzotriazol derivative UV absorbers such as methylene bis-benzotriazolyl tetramethylbutylphenol; triazone derivative UV absorbers such as ethylhexyl triazone; benzylidene camphor derivative UV absorbers such as 3-(4'-methylbenzylidene)-3-pentene-2-on; phenylbenzimidazole derivative UV absorbers; cinnamic acid UV absorbers such as octyl cinnamate, ethyl 4-isopropylcinnamate, ethyl 2,4-diisopropylcinnamate, methyl 2,4-diisopropylcinnamate, propyl p-methoxycinnamate, isopropyl p-methoxycinnamate, isoamyl p-methoxycinnamate, 2-ethoxyethyl p-methoxycinnamate, cyclohexyl p-methoxycinnamate, ethyl α-cyano-β-phenylcinnamate, and 2-ethylhexyl α-cyano-β-phenylcinnamate; benzotriazole derivative UV absorbers such as 2,2'-dihydroxy-5-methylbenzotriazole, 2-(2'-hydroxy-5'-tert-octylphenyl)benzotriazole, and 2-(2'-hydroxy-5'-methylphenyl)benzotriazole; benzalmalonate derivative UV absorbers such as polysilicone-15; urocanic acid; urocanic acid ethyl ester; 2-phenyl-5-methylbenzoxazol; 2-(2'-hydroxy-5'-methylphenyl)benzotriazole; 2-(2-hydroxy-4-isobutoxyphenyl)-2H-benzotriazole; dibenzalazine; dianisoylmethane; and Mexoryl.

In particular, it is preferred that UV absorbers selected from octocrylene, octyl methoxycinnamate, 4-tert-butyl-4'-methoxybenzoylmethane, methylene bis-benzotriazolyl tetramethylbutylphenol, bis-ethylhexyloxyphenol methoxyphenyl triazine; diethylamino hydroxybenzoyl hexyl benzoate; ethylhexyl triazone, phenylbenzimidazole sulfonic acid, dimethicone diethylbenzalmalonate, diethylhexyl butamido triazone, and 2-(4-(2-ethylhexyloxy)-2-hydroxyphenyl)-2H-benzotriazol be used in combination. With use of these absorbers, the sunscreen cosmetic with a high sunscreen effect and an excellent stability over time can be obtained.

The amount of UV absorber is not limited in particular, and the total amount is generally 0.1 to 20% by mass in the cosmetic.

In the composition of the present invention, various kinds of components generally used in cosmetics, such as moisturizers, whitening agents, powders, pH adjusters, neutralizers, antioxidants, preservatives, antibacterial agents, drugs, plant extracts, perfumes, and colorants, can be incorporated so far as the effect of the present invention is not deteriorated.

Examples of moisturizers include polyethylene glycol, propylene glycol, glycerin, 1,3-butylene glycol, xylitol, sorbitol, maltitol, chondroitin sulfate, mucoitin sulfate, charonin acid, atelocollagen, cholesteryl 12-hydroxystearate, sodium lactate, bile acid salts, dl-pyrrolidonecarboxylic acid salts, alkylene oxide derivatives, short-chain soluble collagen, diglycerin (EO) PO adducts, hestnut rose (*Rosa roxburghii* fruit) extract, yarrow (*Achillea millefolium*) extract, melilot extract, amino acid, nucleic acid, proteins such as elastin, and mucopolysaccharides such as hyaluronic acid and chondroitin sulfate.

Examples of whitening agents include salts of L-ascorbic acid and their derivatives, salts of tranexamic acid and their derivatives, salts of alkoxy salicylic acids and their derivatives, and arbutin.

Examples of powders include inorganic powders such as talc, kaolin, mica, sericite, muscovite, phlogopite, synthetic mica, lepidolite, biotite, vermiculite, magnesium carbonate, calcium carbonate, aluminum silicate, barium silicate, calcium silicate, magnesium silicate, strontium silicate, tungstic acid metal salt, magnesium, silica, zeolite, barium sulfate, calcined calcium sulfate (calcined gypsum), calcium phosphate, fluorine apatite, hydroxy apatite, ceramic powder, metallic soaps (e.g., zinc myristate, calcium palmitate and aluminum stearate), and boron nitride; organic powders such as polyamide resin powder (nylon powder), polyethylene powder, acrylic resin powder (e.g., poly methyl methacrylate powder), polystyrene powder, styrene/acrylic acid copolymer resin powder, benzoguanamine resin powder, polytetrafluoroethylene powder, cellulose powder, polymethylsilsesquioxane powder, and silicone elastomer powder; inorganic white pigments such as titanium dioxide and zinc oxide; inorganic red pigments such as iron oxide (red iron oxide) and iron titanate; inorganic brown pigments such as γ-iron oxide; inorganic yellow pigments such as yellow iron oxide and ocher; inorganic black pigments such as black iron oxide and low-order titanium oxide; inorganic purple pigments such as manganese violet and cobalt violet; inorganic green pigments such as chromium oxide, chromium hydroxide, and cobalt titanate; inorganic blue pigments such as ultramarine blue and iron blue; pearl pigments such as titanium oxide coated mica, titanium oxide coated bismuth oxychloride, titanium oxide coated talc, colored titanium oxide coated mica, bismuth oxychloride, and fish scale flakes; metal powder pigments such as aluminum powder and copper powder; organic pigments such as zirconium, barium or aluminum lake (e.g., organic pigments such as red 201, red 202, red 204, red 205, red 220, red 226, red 228, red 405, orange 203, orange 204, yellow 205, yellow 401, and blue 404, as well as red 3, red 104, red 106, red 227, red 230, red 401, red 505, orange 205, yellow 4, yellow 5, yellow 202, yellow 203, green 3, and blue 1); and natural colorants such as chlorophyll and β-carotene.

Also, the examples include UV protective powders such as titanium oxide fine particles and zinc oxide fine particles.

These powders may be hydrophobized or hydrophilized powders depending on the purpose. For hydrophobization, any common method for preparing a hydrophilized powder generally used in cosmetic applications can be used. For example, one or more substances such as higher fatty acids, surfactants (including any of anionic, cationic, and nonionic surfactants), metal soaps, oils and fats, waxes, silicones, fluorides, hydrocarbons, dextrin fatty acid esters can be used. For hydrophilization, any of organic and inorganic treatments can be used. The hydrophilizing agent is not limited in particular, and the examples include polyhydric alcohols, polysaccharides, water-soluble polymers, metal alkoxide, and water glass.

Examples of pH adjusters include lactic acid, citric acid, sodium citrate, glycolic acid, succinic acid, tartaric acid, dl-malic acid, potassium carbonate, sodium hydrogencarbonate, and ammonium hydrogencarbonate.

Examples of antioxidants include ascorbic acid, α-tocopherol, dibutylhydroxytoluene, and butylhydroxyanisole.

Examples of preservatives and antibacterial agents include paraoxybenzoic acid esters, phenoxyethanol, benzoic acid, salicylic acid, phenol, sorbic acid, p-chlorometacresol, hexachlorophene, benzalkonium chloride, chlorhexidine chloride, trichlorocarbanilide, and photosensitizers.

The oil-in-water cosmetic of the present invention can be widely applied in cosmetics, pharmaceuticals, and quasi-drugs which are applied on external skin such as skin and hairs. The product form thereof may be free, and the cosmetic can be used as a milky lotion, cream, emulsified foundation, emulsified sunscreen, and so on. In particular, the cosmetic is preferably used as a sunscreen cosmetic.

Principle

FIG. 1 shows the conception diagrams of the conventional emulsification method using surfactants and the three-phase emulsification method used herein. In the conventional emulsification method using surfactants, as shown in FIG. 1(a), since a surfactant has a hydrophilic group and a lipophilic group, which have different properties from each other, in the molecule, the surfactant sit on the oil particles in the state that the lipophilic group is compatible with oil, and the hydrophilic group is oriented to outside of oil particles. Thus, the oil particles are easily compatible with water and becomes homogenously mixed in water medium to form an O/W emulsion.

Figure 2:
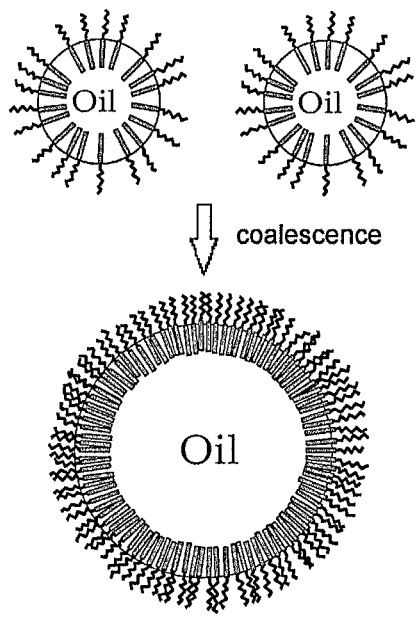
FIG. 2(a) is a diagram illustrating a phenomenon owing to thermal collision in conventional adsorbed-molecule type.
FIG. 2(b) is a diagram illustrating a phenomenon owing to thermal collision in vesicle-particle adhesion type.
Figure 2:
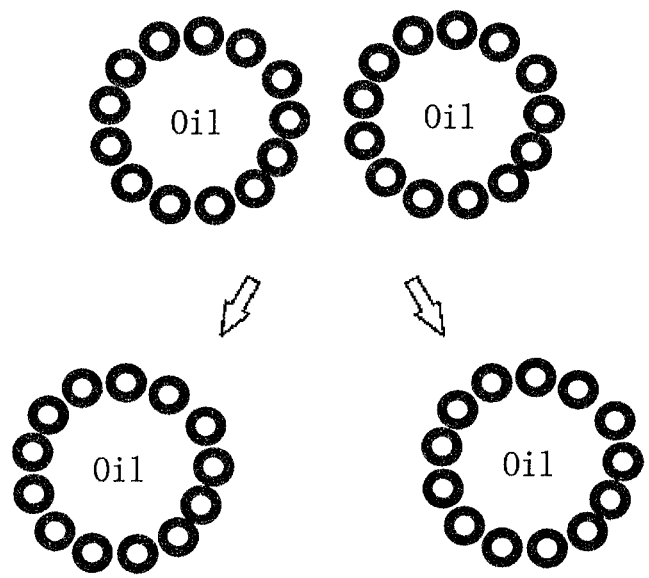

However, according to such a conventional emulsification method, since surfactants adsorb to the surfaces of oils to form a monomolecular emulsion membrane, there is inconvenience that the property of interface is changed depending on the kinds of surfactants. Moreover, as shown in FIG. 2(a), the size of oil droplets becomes increasingly large by coalescence owing to thermal collision between oil droplets, eventually resulting in separation into oil and aqueous solution of surfactant. To prevent such separation, it is necessary to form microemulsion, in which a large amount of surfactants may have to be used.

In the present invention, vesicle particles are adhered to oil particles as an emulsifying and dispersing agent phase (FIG. 1(b)), whereby the three-phase structure of aqueous phase-emulsifying and dispersing agent phase-oil phase is formed to make it difficult to cause coalescence owing to thermal collision without lowering the interfacial energy due to the compatibility (FIG. 2(b)): thus, a long-term stability of emulsion is achieved. In addition, by using a lower alcohol in such a system, the stability of emulsion is further improved. Furthermore, according to the emulsification method of the present invention (i.e., the three-phase emulsification method), based on the above-mentioned mechanism, emulsion can be formed using a small amount of emulsion dispersant.

EXAMPLES

Hereinafter, the present invention will be further explained with reference to specific examples. However, the present invention is not limited by these examples. The amount (%) is expressed in mass % unless otherwise specified.

<Stability Evaluation of Emulsion Particles with Lower Alcohol>

(Production Method)

Based on the formulations in Table 1, oil-in-water cosmetics were produced in the following method.

Polyoxyethylene hydrogenated caster oil derivative, which is an amphiphilic substance, was added to and mixed with the aqueous phase described in the following Table 1, and the mixture was treated with a homomixer for 1 minute to prepare an aqueous phase part containing vesicle particles. The oil component to be emulsified in Table 1, which had been homogeneously mixed in advance, was gradually added to the obtained aqueous phase part while stirred with a homomixer to obtain an oil-in-water cosmetic.

(Evaluation Method)

Each composition of these examples was put into a 50 ml sample tube (diameter: 3 cm), a test of rotating the tube at 45 rpm at room temperature for 4 hours was conducted, and the emulsification degree of the emulsified composition was judged by visually observing the presence or absence of oil floating. The average particle size of vesicle particles in the vesicle dispersion was measured in a dynamic light scattering method using a particle-size distribution measurement device FPAR-1000 (manufactured by Otsuka Electronics Co., Ltd.), and the emulsion particle size was measured by directly observing with an optical microscope (BX51 manufactured by Olympus Corporation).

Evaluation Criteria for Emulsion Stability of Emulsified Composition

O: Oil floating was not observed visually.
Δ: Slight oil floating was observed visually.
X: Substantial amount of oil floating was observed visually.

TABLE 1

|  |  | Example | | | | |
|---|---|---|---|---|---|---|
|  |  | 1-1 | 1-2 | 1-3 | 1-4 | 1-5 |
| Aqueous phase | Ion-exchanged water | Balance | Balance | Balance | Balance | Balance |
|  | Ethanol | — | 2 | 4 | 8 | 15 |
|  | Carboxyvinyl polymer | 0.12 | 0.12 | 0.12 | 0.12 | 0.12 |
|  | Neutralizer | Q.S. | Q.S. | Q.S. | Q.S. | Q.S. |
|  | Preservative | Q.S. | Q.S. | Q.S. | Q.S. | Q.S. |
| Amphiphilic substance | Polyoxyethylene (10) hydrogenated caster oil | 3 | 3 | 3 | 3 | 3 |
| Oil component to be emulsified | Octocrylene | 5 | 5 | 5 | 5 | 5 |
|  | Octyl methoxycinnamate | 5 | 5 | 5 | 5 | 5 |
|  | t-Butyl methoxydibenzoylmethane | 2 | 2 | 2 | 2 | 2 |
|  | Dimethicone | 2 | 2 | 2 | 2 | 2 |
| Evaluation | Average particle size of vesicles (nm) | 410 | 300 | 380 | 335 | 300 |
|  | Emulsion particle size (μm) | 1 to 20 | 1 to 15 | 1 to 12.5 | 1 to 7.5 | 1 to 3 |
|  | Emulsion particle stability | X | Δ | Δ | O | O |

As shown in Table 1, in Example 1-1 containing no ethanol at all and also in Examples 1-2 to 1-5 containing each amount of ethanol, there was no large difference in the average particle size of vesicles formed of polyoxyethylene (10) hydrogenated caster oil contained in the aqueous phase part. However, the emulsion stability was improved as the amount of ethanol was increased, and especially a significantly enhanced effect was achieved when ethanol was 5% by mass or more in the cosmetic.

Though the reason why the stability is improved by incorporating ethanol is not clear, for one, it can be thought that the strength of vesicle particles and the adherence of vesicle particles to oil droplet particles is enhanced by ethanol, whereby the coalescence of emulsion particles is further inhibited.

Since a large amount of ethanol in an emulsified composition had been thought to significantly lower emulsion stability in the conventional knowledge, the above-mentioned result that the stability of emulsified composition is improved by incorporating ethanol was surprising.

Also, it became clear that the particle size of emulsified composition becomes smaller as the amount of ethanol is increased.

Figure 3:
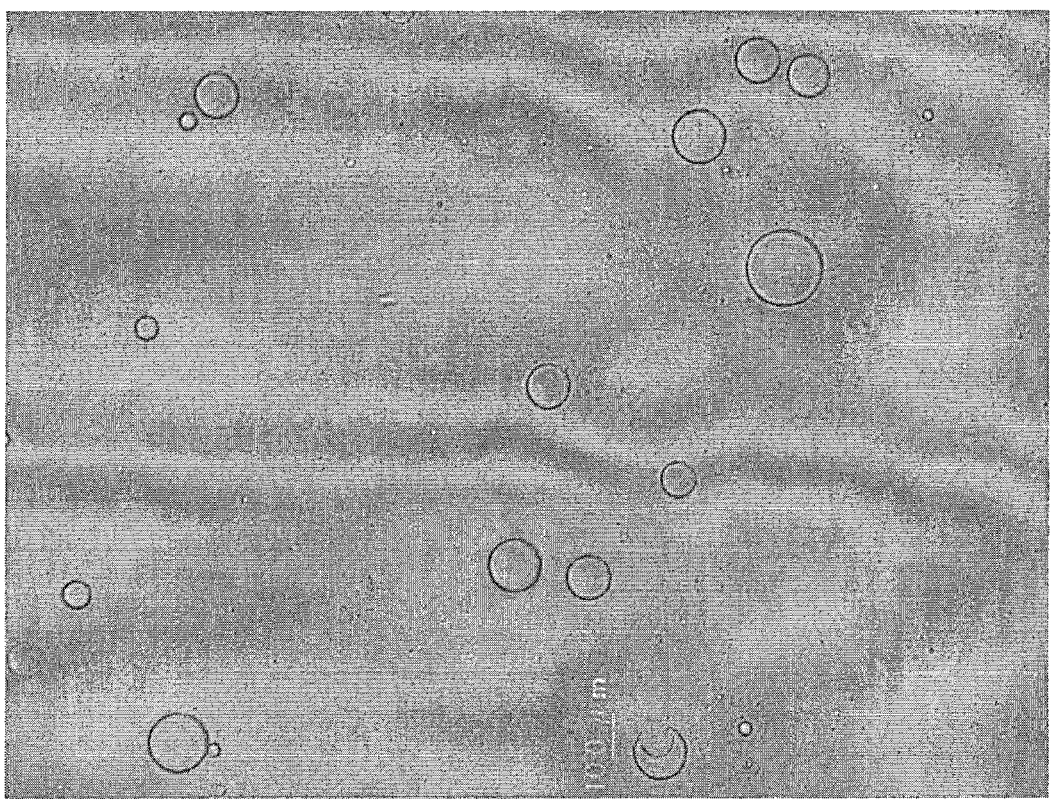
FIG. 3 is an optical photomicrograph of a three-phase emulsified composition without a lower alcohol (ethanol).
Figure 4:
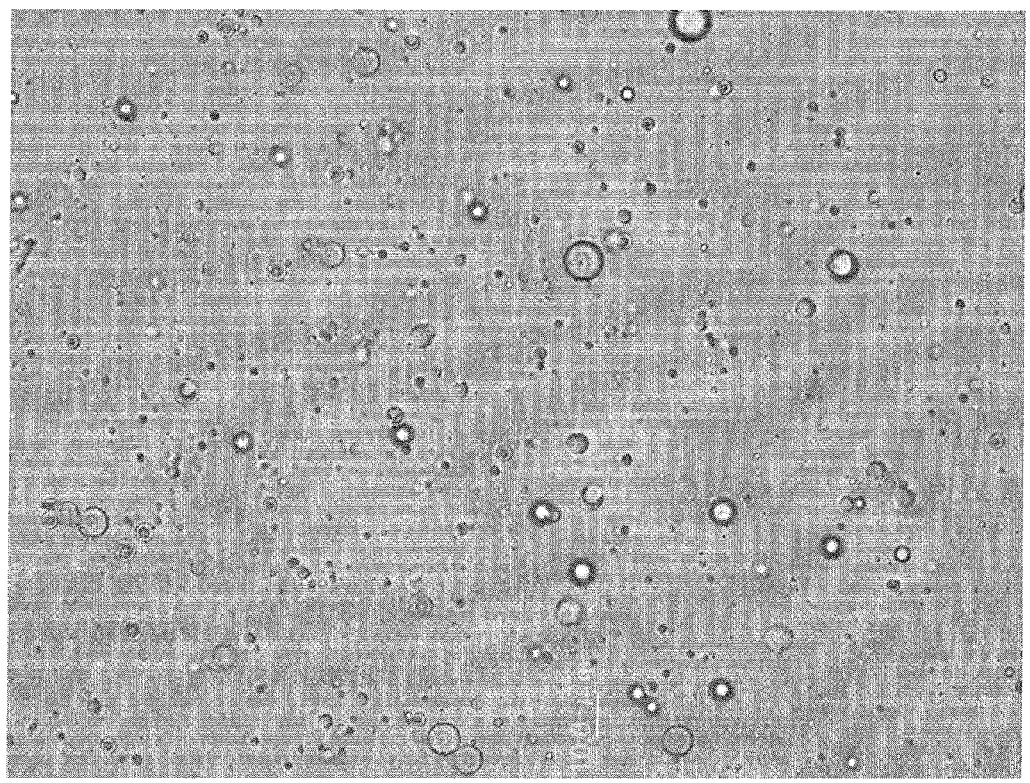
FIG. 4 is an optical photomicrograph of a three-phase emulsified composition containing 2% of lower alcohol (ethanol).
Figure 5:
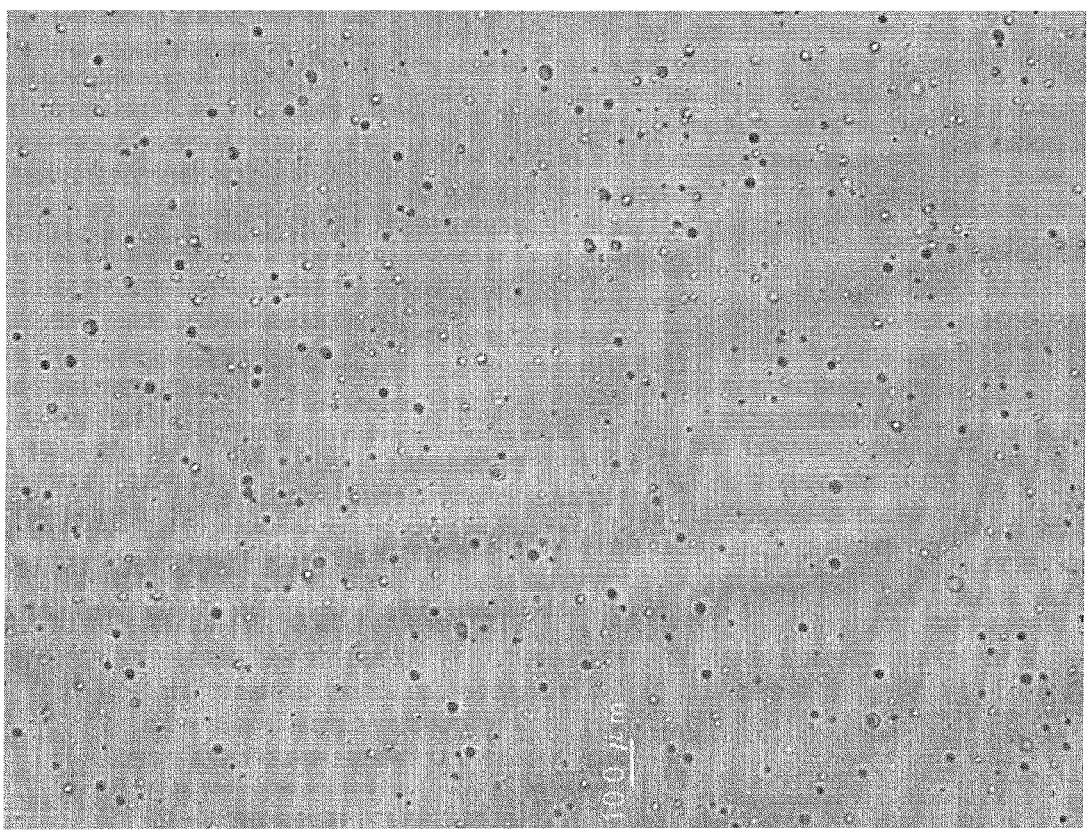
FIG. 5 is an optical photomicrograph of a three-phase emulsified composition containing 15% of lower alcohol (ethanol).

The optical micrographs of the oil-in-water cosmetics obtained in Examples 1-1, 1-2, and 1-5 in Table 1 are shown in FIGS. 3 to 5 respectively. From each of the optical micrographs, it can be understood that the emulsion particle size becomes small when ethanol is incorporated.

<Study for Vesicle Particle Formation with EO Average Addition Mole Number>

Next, to study the EO average addition mole number suitable for formulation of vesicle particles of polyoxyethylene hydrogenated caster oil in water, polyoxyethylene hydrogenated caster oil was dispersed in an aqueous phase with a homomixer to prepare a dispersion, and the appearance thereof was observed.

As shown in Table 2, when the polyoxyethylene hydrogenated caster oil derivative with EO average addition mole number of 7 was used (Example 2-1), the polyoxyethylene hydrogenated caster oil, which is an amphiphilic substance, was not dispersed in the aqueous phase at all, and it was observed to be floating in the upper layer.

On the other hand, when polyoxyethylene hydrogenated caster oil derivatives with EO average addition mole number of 30, 40, and 60 were used (Examples 2-4 to 2-6), the appearance became translucent, and the average particle size became so fine to be 10 nm or less.

Also, when polyoxyethylene hydrogenated caster oil derivatives with EO average addition mole number of 10 to 20 were used (Examples 2-2 to 2-3), the appearance was white turbid to translucent, and the particle size was 30 to 200 nm.

<Study for Emulsion Particle Stability with EO Addition Mole Number>

Furthermore, to study a suitable EO addition mole number of the polyoxyethylene hydrogenated caster oil derivative in the oil-in-water cosmetic of the present invention, oil-in-water cosmetics (Examples 3-1 to 3-6) were prepared in the production method same with the above-mentioned examples based on the formulations in Table 3. The emulsion particle size of composition in each example was measured, and furthermore the usability was evaluated. Also, the emulsion stability after still standing for 1 month from the production, and the emulsion stability by rolling as conducted in Table 1 were visually evaluated. The measurement of emulsion particle size was directly observed with an optical microscope (BX51 manufactured by Olympus Corporation).

Evaluation Criteria for Usability

O: The composition provided a light feeling in use and quick finish after application on skin.

Δ: The composition provided a slightly light feeling and a slightly slimy feeling in use.

X: The composition provided a sticky feeling and a slimy feeling in use.

The evaluation results for each example are shown in Table 3.

TABLE 2

| | | | Example | | | |
|---|---|---|---|---|---|---|
| | 2-1 | 2-2 | 2-3 | 2-4 | 2-5 | 2-6 |
| Ion-exchanged water | Balance | Balance | Balance | Balance | Balance | Balance |
| Ethanol | 10 | 10 | 10 | 10 | 10 | 10 |
| Polyoxyethylene (7) hydrogenated caster oil | 3 | — | — | — | — | — |
| Polyoxyethylene (10) hydrogenated caster oil | — | 3 | — | — | — | — |
| Polyoxyethylene (20) hydrogenated caster oil | — | — | 3 | — | — | — |
| Polyoxyethylene (30) hydrogenated caster oil | — | — | — | 3 | — | — |
| Polyoxyethylene (40) hydrogenated caster oil | — | — | — | — | 3 | — |
| Polyoxyethylene (60) hydrogenated caster oil | — | — | — | — | — | 3 |
| Evaluation Average particle size of vesicles (nm) | — | 200 | 30 | 10 | 10 | Un-measurable |
| Appearance | — | White-turbid | Translucent | Translucent | Translucent | Translucent |

TABLE 3

| | | \multicolumn{6}{c|}{Example} |
|---|---|---|---|---|---|---|---|
| | | 3-1 | 3-2 | 3-3 | 3-4 | 3-5 | 3-6 |
| Aqueous phase | Ion-exchanged water | Balance | Balance | Balance | Balance | Balance | Balance |
| | Ethanol | 10 | 10 | 10 | 10 | 10 | 10 |
| | Carboxyvinyl polymer | 0.12 | 0.12 | 0.12 | 0.12 | 0.12 | 0.12 |
| | PEG/PPG-17/4 dimethyl ether | 5 | 5 | 5 | 5 | 5 | 5 |
| | Neutralizer | Q.S. | Q.S. | Q.S. | Q.S. | Q.S. | Q.S. |
| | Preservative | Q.S. | Q.S. | Q.S. | Q.S. | Q.S. | Q.S. |
| Amphiphilic substance | Polyoxyethylene (10) hydrogenated caster oil | 3 | — | — | — | — | 1.5 |
| | Polyoxyethylene (20) hydrogenated caster oil | — | 3 | — | — | — | 1.5 |
| | Polyoxyethylene (30) hydrogenated caster oil | — | — | 3 | — | — | — |
| | Polyoxyethylene (40) hydrogenated caster oil | — | — | — | 3 | — | — |
| | Polyoxyethylene (60) hydrogenated caster oil | — | — | — | — | 3 | — |
| Oil component to be emulsified | Octocrylene | 5 | 5 | 5 | 5 | 5 | 5 |
| | Octyl methoxycinnamate | 5 | 5 | 5 | 5 | 5 | 5 |
| | t-Butyl methoxydibenzoylmethane | 2 | 2 | 2 | 2 | 2 | 2 |
| | Dimethicone | 2 | 2 | 2 | 2 | 2 | 2 |
| Evaluation | Emulsion particle size(μm) | 1 to 5 | 1 to 5 | 1 to 10 | 1 to 15 | 1 to 20 | 1 to 5 |
| | Usability | ○ | ○ | Δ | X | X | ○ |
| | Emulsion stability (still standing for IM) | ○ | Δ | Δ to X | Δ to X | X | ○ |
| | Emulsion stability (rolling test) | ○ | Δ | X | X | X | ○ |

From Table 3, when the polyoxyethylene hydrogenated caster oil with EO average addition mole number of 30, 40, or 60 was used (Examples 3-3 to 3-5), the emulsion particle size was large, the usability tended to be poor, and oil floating was observed.

On the other hand, in Example 3-2 containing the polyoxyethylene hydrogenated caster oil derivative with EO average addition mole number of 20, oil floating was slightly observed, but the emulsion particle size was so small to be 1 to 5 μm, and an emulsified composition with an excellent usability could be obtained.

In Example 3-1 containing the polyoxyethylene hydrogenated caster oil derivative with EO average addition mole number of 10, the emulsion particle size was so small to be 1 to 5 μn, the composition provided the usability of light feeling and quick finish on skin, and oil floating was not observed.

Furthermore, in Example 3-6 containing the polyoxyethylene hydrogenated caster oil derivatives with EO average addition mole numbers of 10 and 20 in combination, the emulsion particle size was so small to be 1 to 5 μn, the composition provided the usability of light feeling and quick finish on skin, and oil floating was not observed.

From these results, it became clear that the EO average addition mole number of the polyoxyethylene hydrogenated caster oil derivative is preferably 10 to 20.

<Study for Thickener>

Based on the formulations in Table 4, oil-in-water cosmetics (Examples 4-1 to 4-7) were prepared in the production method same with the above-mentioned examples, and the emulsion particle size of each composition was measured. Also, the test for emulsion stability was conducted in the same manner with that in Table 1, to judge the emulsification degree of the emulsified composition by visually observing the presence or absence of oil floating.

TABLE 4

| | | \multicolumn{7}{c|}{Example} |
|---|---|---|---|---|---|---|---|---|
| | | 4-1 | 4-2 | 4-3 | 4-4 | 4-5 | 4-6 | 4-7 |
| Aqueous phase | Ion-exchanged water | Balance | Balance | Balance | Balance | Balance | Balance | Balance |
| | Ethanol | 10 | 10 | 10 | 10 | 10 | 10 | 10 |
| | Tamarind gum | 0.1 | — | — | — | — | — | — |
| | Succinoglycan | — | 0.1 | — | — | — | — | — |
| | Hydroxyethyl cellulose | — | — | 0.1 | — | — | — | — |
| | Hydroxypropyl cellulose | — | — | — | 0.1 | — | — | — |
| | Xanthan gum | — | — | — | — | 0.1 | — | 0.3 |
| | Carboxyvinyl polymer | 0.12 | 0.12 | 0.12 | 0.12 | 0.12 | 0.12 | — |
| | PEG/PPG-17/4 dimethyl ether | 5 | 5 | 5 | 5 | 5 | 5 | 5 |
| | Neutralizer | Q.S. | Q.S. | Q.S. | Q.S. | Q.S. | Q.S. | Q.S. |
| | Preservative | Q.S. | Q.S. | Q.S. | Q.S. | Q.S. | Q.S. | Q.S. |

TABLE 4-continued

|  |  | Example | | | | | | |
|---|---|---|---|---|---|---|---|---|
|  |  | 4-1 | 4-2 | 4-3 | 4-4 | 4-5 | 4-6 | 4-7 |
| Amphiphilic substance | Polyoxyethylene (10) hydrogenated caster oil | 3 | 3 | 3 | 3 | 3 | 3 | 3 |
| Oil component to be emulsified | Octocrylene | 5 | 5 | 5 | 5 | 5 | 5 | 5 |
|  | Octyl methoxycinnamate | 5 | 5 | 5 | 5 | 5 | 5 | 5 |
|  | t-Butyl methoxy-dibenzoylmethane | 2 | 2 | 2 | 2 | 2 | 2 | 2 |
|  | Dimethicone | 3 | 3 | 3 | 3 | 3 | 3 | 3 |
| Evaluation | Emulsion particle size (μm) | 1 to 5 | up to 2.5 | up to 2.5 | up to 2.5 | up to 2.5 | up to 2.5 | up to 2.5 |
|  | Emulsion particle stability (RT) | Δ | ○ | ○ | ○ | ○ | ○ | ○ |
|  | Emulsion particle stability (50° C.) | X | ○ | ○ | ○ | ○ | Δ | ○ |

As is clear from Table 4, when carboxyvinyl polymer, succinoglycan, hydroxyethyl cellulose, hydroxypropyl cellulose, or xanthan gum was used as a thickener, oil floating was not observed in particular, and the emulsion stability was good. On the other hand, when the other thickeners were used, oil floating was sometimes distinct.

<Study for Emulsification Method> gradually added to the aqueous phase part, which had been homogeneously mixed in advance, while stirred with a homomixer to obtain oil-in-water cosmetics.

As is clear from Table 5, in the oil-in-water cosmetic produced in the three-phase emulsification method (Process A), when the polyoxyethylene hydrogenated caster oil with EO average addition mole number of 10 to 20 was used, the

TABLE 5

|  |  | Example | | | | | | | |
|---|---|---|---|---|---|---|---|---|---|
|  |  | 5-1 | 5-2 | 5-3 | 5-4 | 5-5 | 5-6 | 5-7 | 5-8 |
| Aqueous phase | Ion-exchanged water | Balance | Balance | Balance | Balance | Balance | Balance | Balance | Balance |
|  | Ethanol | 10 | 10 | — | — | 10 | 10 | — | — |
|  | Carboxyvinyl polymer | 0.12 | 0.12 | 0.12 | 0.12 | 0.12 | 0.12 | 0.12 | 0.12 |
|  | PEG/PPG-17/4 dimethyl ether | 5 | 5 | 5 | 5 | 5 | 5 | 5 | 5 |
|  | Neutralizer | Q.S. | Q.S. | Q.S. | Q.S. | Q.S. | Q.S. | Q.S. | Q.S. |
|  | Preservative | Q.S. | Q.S. | Q.S. | Q.S. | Q.S. | Q.S. | Q.S. | Q.S. |
| Amphiphilic substance | POE(10) hydrogenated caster oil | 3 | — | 3 | — | 3 | — | 3 | — |
|  | POE(60) hydrogenated caster oil | — | 3 | — | 3 | — | 3 | — | 3 |
| Oil component to be emulsified | Octocrylene | 5 | 5 | 5 | 5 | 5 | 5 | 5 | 5 |
|  | Octyl methoxycinnamate | 7.5 | 7.5 | 7.5 | 7.5 | 7.5 | 7.5 | 7.5 | 7.5 |
|  | t-Butyl methoxy-dibenzoylmethane | 2 | 2 | 2 | 2 | 2 | 2 | 2 | 2 |
|  | Dimethicone | 2 | 2 | 2 | 2 | 2 | 2 | 2 | 2 |
| Production process *1 |  | A | | | | B | | | |
| Evaluation | Emulsion particle size (nm) | 1 to 5 | 1 to 20 | 1 to 20 | 1 to 50 | 1 to 5 | 1 to 10 | 1 to 10 | 1 to 5 |
|  | Usability | ○ | X | Δ | X | Δ | X | X | X |
|  | Emulsion particle stability | ○ | X | X | X | X | X | X | ○ |

*1: Production Process

Process A (Three-Phase Emulsification Method):

Polyoxyethylene hydrogenated caster oil was added to and mixed with the aqueous phase, and the mixture was treated with a homomixer for 1 minute to prepare an aqueous phase part containing vesicle particles. The oil components to be emulsified, which had been homogeneously mixed in advance, was gradually added to the obtained aqueous phase part while stirred with a homomixer to obtain oil-in-water cosmetics.

Process B:

Polyoxyethylene hydrogenated caster oil was mixed with the oil components to be emulsified, and the mixture was emulsion stability was improved with the use of ethanol (Example 5-1 vs. Example 5-3).

To the contrary, even in the production by the three-phase emulsification method, when the polyoxyethylene hydrogenated caster oil with EO average addition mole number of more than 20 was used, the emulsion stability could not be improved even with the use of ethanol (Example 5-2 vs. Example 5-4).

On the other hand, when a composition was produced by Process B, which is a conventional emulsification method, an oil-in-water cosmetic with a good emulsion stability could be obtained by using the polyoxyethylene hydrogenated caster oil with EO average addition mole number suitable for emulsification (e.g., 60 mole). However, the emulsion stability became significantly deteriorated when ethanol was used (Example 5-6 vs. Example 5-8). Furthermore, in the production by a conventional emulsification method, even when the EO average addition mole number was in the range of 10 to 20, an oil-in-water cosmetic with a good emulsion stability could not be obtained regardless of the presence or absence of ethanol (Examples 5-5 and 5-7).

From the results, it became clear that the oil-in-water cosmetic with a good emulsion stability can be obtained by mixing the oil component to be emulsified with the aqueous phase in which a lower alcohol coexists in a vesicle dispersion of the polyoxyethylene hydrogenated caster oil with EO average addition mole number of 10 to 20.

Hereinafter, preferable examples of the cosmetics of the present invention will be shown. However, the present invention is not limited to these formulation examples in any manner.

Formulation Example 1

Sun-Cut Oil-In-Water Milky Lotion

| | |
|---|---|
| (1) Polyoxyethylene (10) hydrogenated caster oil | 3.0 |
| (2) Dimethicone | 3.0 |
| (3) Octocrylene | 5.0 |
| (4) Octyl methoxycinnamate | 5.0 |
| (5) t-Butyl methoxydibenzoylmethane | 2.0 |
| (6) Diethylhexyl succinate | 2.0 |
| (7) Diisopropyl sebacate | 1.0 |
| (8) Succinoglycan | 0.05 |
| (9) Xanthan gum | 0.1 |
| (10) Hydroxyethyl cellulose | 0.01 |
| (11) Carboxyvinyl polymer | 0.1 |
| (12) Tranexamic acid | 1.0 |
| (13) Dipropylene glycol | 5.0 |
| (14) Chelating agent | Q.S. |
| (15) Preservative | Q.S. |
| (16) Perfume | Q.S. |
| (17) Ethanol | 10.0 |
| (18) Purified water | Balance |

(Production Method)
(1) and (17) to (18) were mixed and stirred with a homomixer, (8) to (15) were further added to and mixed with the mixture, and then (2) to (7) and (16) were added thereto while stirred with a homomixer.

Formulation Example 2

Essence

| | |
|---|---|
| A. Aqueous phase part | |
| (1) Polyoxyethylene (10) hydrogenated caster oil | 3.0 |
| (2) 1,3-Butylene glycol | 10.0 |
| (3) Glycerin | 10.0 |
| (4) Sorbitol | 3.0 |
| (5) Polyethylene glycol 1000 | 2.0 |
| (6) Quince seed extract | 0.5 |
| (7) Hyaluronic acid | 0.001 |
| (8) Salicylic acid | 0.1 |
| (9) Ethanol | 5.0 |
| (10) Carboxyvinyl polymer | 0.1 |
| (11) Alkyl-modified carboxyvinyl polymer (PEMULEN TR-2) | 0.08 |
| (12) Preservative | Q.S. |
| (13) Chelating agent | Q.S. |
| (14) Buffer | Q.S. |
| (15) Purified water | Balance |
| B. Oil phase part | |
| (16) Dimethicone copolyol | 0.1 |
| (17) Liquid paraffin | 2.0 |
| (18) Isostearic acid | 0.01 |
| (19) Dimethylpolysiloxane | 2.0 |
| (20) Ubiquinone | 0.03 |
| (21) Vitamin E acetate | 0.05 |
| (22) Perfume | Q.S. |
| C. Neutralizer | |
| (23) Potassium hydroxide | Q.S. |

(Production Method)
At room temperature, (6) was mixed with and homogeneously dissolved in (15), then the other aqueous phase part components were added thereto, and the mixture was stirred sufficiently to obtain Phase A (aqueous phase part). Phase A was mixed with Phase B (oil phase part), which had been prepared in advance, the mixture was treated with a homomixer to homogenize emulsion particles. Then, the emulsion was neutralized with the neutralizer (23).

Formulation Example 3

Oil-In-Water Emulsion Foundation

| | |
|---|---|
| (1) Polyoxyethylene (20) hydrogenated caster oil | 2.0 |
| (2) Ethanol | 7.0 |
| (3) 1,3-Butylene glycol | 5.0 |
| (4) Glycerin | 3.0 |
| (5) Dimethylpolysiloxane | 8.0 |
| (6) Cetyl 2-ethylhexanoate | 5.0 |
| (7) Decamethylcyclopentasiloxane | 5.0 |
| (8) 2-Ethylhexyl p-methoxycinnamate | 5.0 |
| (9) DL-α-tocopherol acetate | 0.1 |
| (10) Titanium oxide | 4.0 |
| (11) Kaolin | 3.0 |
| (12) Silicic anhydride | 5.0 |
| (13) Sodium hyaluronnate | 0.1 |
| (14) Red iron oxide | Q.S. |
| (15) Yellow iron oxide | Q.S. |
| (16) Black iron oxide | Q.S. |
| (17) Xanthan gum | 0.1 |
| (18) Paraoxybenzoic acid ester | Q.S. |
| (19) Perfume | Q.S. |
| (20) Purified water | Balance |

(Production Method)
(1) to (4), (10) to (18), and (20) were mixed and stirred with a homomixer. Then, the mixture was added to the oil phase, which had been prepared by mixing (5) to (9) and (19), while stirred with a homomixer.

Formulation Example 4

Sunscreen Milky Lotion

| | |
|---|---|
| A. Aqueous phase part | |
| Ion-exchanged water | Balance |
| Ethanol | 10 |
| Agar | 0.1 |
| Carboxyvinyl polymer | 0.12 |
| PEG/PPG-17/4 dimethyl ether | 5 |

-continued

| | |
|---|---|
| Neutralizer | Q.S. |
| Preservative | Q.S. |
| B. Amphiphilic substance | |
| Polyoxyethylene (10) hydrogenated caster oil | 3 |
| C. Oil component to be emulsified | |
| Octocrylene | 5 |
| Octyl methoxycinnamate | 5 |
| t-Butyl methoxydibenzoylmethane | 2 |
| Dimethicone | 3 |

(Production Method)

The amphiphilic substance was added to and mixed with the aqueous phase, and the mixture was treated with a homomixer for 1 minute to prepare the aqueous phase part containing vesicle particles. The oil component to be emulsified, which had been homogeneously mixed in advance, was gradually added to the obtained aqueous phase part while stirred with a homomixer to obtain the oil-in-water cosmetic.

All cosmetics of the above-mentioned formulation examples provided a light fresh feeling in use and were excellent in emulsion stability.

Formulation Example 5

Sunscreen Milky Lotion

| | |
|---|---|
| (1) Polyoxyethylene (10) hydrogenated caster oil | 3.0 |
| (2) Ethylhexyl isononanoate (IOB = 0.2) | 3.0 |
| (3) Decamethylcyclopentasiloxane | 2.0 |
| (4) Octocrylene | 4.0 |
| (5) t-Butyl methoxydibenzoylmethane | 2.0 |
| (6) Di-2-ethylhexyl succinate (IOB = 0.32) | 2.0 |
| (7) Isohexadecane | 1.0 |
| (8) Succinoglycan | 0.05 |
| (9) Xanthan gum | 0.1 |
| (10) Hydroxyethyl cellulose | 0.01 |
| (11) Acrylamide/AMPS copolymer (effective portion: 40%) | 1.0 |
| (Product name: Sepigel 305, manufactured by SEPPIC) | |
| (12) Tranexamic acid | 1.0 |
| (13) Dipropylene glycol | 4.0 |
| (14) Edetate | 0.01 |
| (15) Phenoxy ethanol | 0.5 |
| (16) Perfume | 0.1 |
| (17) Ethanol | 9.0 |
| (18) Purified water | Balance |

(Production Method)

(1), (17), and (18) were mixed and stirred with a homomixer, and then (2) to (7) and (16) were added thereto while stirred with a homomixer. Then, (8) to (15) were added to the mixture to obtain the desired sunscreen milky lotion.

Formulation Example 6

Anti-Aging Essence

| | |
|---|---|
| A. Aqueous phase part | |
| (1) Polyoxyethylene (10) hydrogenated caster oil | 3.0 |
| (2) 1,3-Butylene glycol | 5.0 |
| (3) Glycerin | 7.0 |
| (4) Xylitol | 3.0 |
| (5) Polyethylene glycol 1000 | 2.0 |
| (6) Piperidine propionic acid | 1.0 |
| (7) Green tea extract | 0.1 |

-continued

| | |
|---|---|
| (8) Yeast extract | 0.1 |
| (9) Hyaluronic acid | 0.1 |
| (10) Vinyl pyrrolidone/AMPS copolymer | 0.8 |
| (Product name: ARISTOFLEX AVC, manufactured by CLARIANT) | |
| (11) Alkyl-modified carboxyvinyl polymer | 0.08 |
| (Product name: Pemulen TR-2, manufactured by Lubrizol Corporation) | |
| (12) Methyl paraben | 0.1 |
| (13) Edetate | 0.05 |
| (14) Phenoxy ethanol | 0.3 |
| (15) Ethanol | 5.0 |
| (16) Purified water | Balance |
| B. Oil phase part | |
| (17) Dimethicone 20 mPa·s | 1.0 |
| (18) α-Olefine oligomer | 1.0 |
| (19) Isodecyl benzoate (IOB = 0.23) | 4.0 |
| (20) Decamethylcyclopentasiloxane | 2.0 |
| (21) Vitamin E acetate | 0.1 |
| (22) Vitamin A palmitate | 0.1 |
| (23) Perfume | Q.S. |
| C. Neutralizer | |
| (24) Potassium hydroxide | Q.S. |

(Production Method)

At room temperature, (1) was mixed with (15) and (16), the mixture was homogeneously stirred with a homomixer to prepare vesicle particles, and then mixed with Phase B (oil phase part), which had been prepared in advance. The mixture was treated with a homomixer to homogenize emulsion particles, and then the other aqueous phase components were added thereto. Finally the neutralizer (24) was added to the emulsion to obtain the desired anti-aging essence.

Formulation Example 7

Whitening Essence

| | |
|---|---|
| A. Aqueous phase part | |
| (1) Polyoxyethylene (10) hydrogenated caster oil | 3.0 |
| (2) Dipropylene glycol | 2.0 |
| (3) 1,3-Butylene glycol | 3.0 |
| (4) Glycerin | 7.0 |
| (5) Erythritol | 3.0 |
| (6) Polyethylene glycol 1000 | 2.0 |
| (7) Ascorbyl glucoside | 2.0 |
| (8) Magnesium ascorbyl phosphate | 0.1 |
| (9) Morus alba root extract | 0.2 |
| (10) Bergenia ligulata root extract | 0.2 |
| (11) Saxifraga extract | 0.2 |
| (12) Hyaluronic acid | 0.1 |
| (13) Dimethylacrylamide/AMPS crosspolymer | 2.0 |
| (Product name: SUpolymer G-1, manufactured by Toho Chemical Industry Co., Ltd.) | |
| (14) Alkyl-modified carboxyvinyl polymer | 0.08 |
| (Product name: Pemulen TR-2, manufactured by Lubrizol Corporation) | |
| (15) Methyl paraben | 0.1 |
| (16) Edetate | 0.05 |
| (17) Phenoxy ethanol | 0.3 |
| (18) Ethanol | 9.0 |
| (19) Purified water | Balance |
| B. Oil phase part | |
| (20) Isododecane | 1.0 |
| (21) Liquid paraffin | 1.0 |
| (22) Isodecyl neopentanoate (IOB = 0.2) | 5.0 |
| (23) Decamethylcyclopentasiloxane | 1.0 |
| (24) Perfume | Q.S. |
| C. Neutralizer | |
| (25) Potassium hydroxide | Q.S. |

(Production Method)

At room temperature, (1) mixed with (18) and (19) was homogeneously stirred with a homomixer to prepare vesicle particles, and then mixed with Phase B (oil phase part), which had been prepared in advance. The mixture was treated with a homomixer to homogenize emulsion particles, and the other aqueous phase components were added thereto. Finally, the neutralizer (25) was added to the emulsion to obtain the desired whitening essence.

All of the oil-in-water cosmetics of Formulation Examples 5 to 7 were excellent in emulsion stability and usability (spreadability, finish on skin, non-stickiness, and elasticity).

Formulation Example 8

Sunscreen Milky Lotion

| | |
|---|---|
| (1) Polyoxyethylene (10) hydrogenated castor oil | 3.0 |
| (2) Ethylhexyl isononanoate (IOB = 0.2) | 3.0 |
| (3) Decamethylcyclopentasiloxane | 2.0 |
| (4) Octocrylene | 4.0 |
| (5) t-Butyl methoxydibenzoylmethane | 2.0 |
| (6) Di-2-ethylhexyl succinate (IOB = 0.32) | 2.0 |
| (7) Isohexadecane | 1.0 |
| (8) Succinoglycan | 0.05 |
| (9) Xanthan gum | 0.1 |
| (10) Hydroxyethyl cellulose | 0.01 |
| (11) Carboxyvinyl polymer | 0.1 |
| (12) Tranexamic acid | 1.0 |
| (13) Dipropylene glycol | 4.0 |
| (14) Edetate | 0.01 |
| (15) Phenoxy ethanol | 0.5 |
| (16) Perfume | 0.1 |
| (17) Ethanol | 9.0 |
| (18) Purified water | Balance |

(Production Method)

(1), (17), and (18) were mixed and stirred with a homomixer, (8) to (15) were further added to and mixed with the mixture, and (2) to (7) and (16) were added thereto while stirred with a homomixer.

Formulation Example 9

Anti-Aging Essence

| | |
|---|---|
| A. Aqueous phase part | |
| (1) Polyoxyethylene (10) hydrogenated castor oil | 3.0 |
| (2) 1,3-Butylene glycol | 5.0 |
| (3) Glycerin | 7.0 |
| (4) Xylitol | 3.0 |
| (5) Polyethylene glycol 1000 | 2.0 |
| (6) Piperidine propionic acid | 1.0 |
| (7) Green tea extract | 0.1 |
| (8) Yeast extract | 0.1 |
| (9) Hyaluronic acid | 0.1 |
| (10) Carboxyvinyl polymer | 0.1 |
| (11) Alkyl-modified carboxyvinyl polymer | 0.08 |
| (Product name: Pemulen TR-2, manufactured by Lubrizol Corporation) | |
| (12) Methyl paraben | 0.1 |
| (13) Edetate | 0.05 |
| (14) Phenoxy ethanol | 0.3 |
| (15) Ethanol | 5.0 |
| (16) Purified water | Balance |
| B. Oil phase part | |
| (17) Dimethicone 20 mPa·s | 1.0 |
| (18) α-Olefine oligomer | 1.0 |
| (19) Isodecyl benzoate (IOB = 0.23) | 4.0 |

| | |
|---|---|
| (20) Decamethylcyclopentasiloxane | 2.0 |
| (21) Vitamin E acetate | 0.1 |
| (22) Vitamin A palmitate | 0.1 |
| (23) Perfume | Q.S. |
| C. Neutralizer | |
| (24) Potassium hydroxide | Q.S. |

(Production Method)

At room temperature, (1) mixed with (15) and (16) was homogeneously stirred with a homomixer to prepare vesicle particles, and then the other aqueous phase components were added thereto. The mixture was stirred sufficiently with to obtain Phase A (aqueous phase part). Phase A was mixed with Phase B (oil phase part), which had been prepared in advance, and the mixture was treated with a homomixer to homogenize emulsion particles. Then, the neutralizer (24) was added thereto.

Formulation Example 10

Whitening Essence

| | |
|---|---|
| A. Aqueous phase part | |
| (1) Polyoxyethylene (10) hydrogenated castor oil | 3.0 |
| (2) Dipropylene glycol | 2.0 |
| (3) 1,3-Butylene glycol | 3.0 |
| (4) Glycerin | 7.0 |
| (5) Erythritol | 3.0 |
| (6) Polyethylene glycol 1000 | 2.0 |
| (7) Ascorbyl glucoside | 2.0 |
| (8) Magnesium ascorbyl phosphate | 0.1 |
| (9) Morus alba root extract | 0.2 |
| (10) Bergenia ligulata root extract | 0.2 |
| (11) Saxifraga extract | 0.2 |
| (12) Hyaluronic acid | 0.1 |
| (13) Xanthan gum | 0.15 |
| (14) Alkyl-modified carboxyvinyl polymer | 0.08 |
| (Product name: Pemulen TR-2, manufactured by Lubrizol Corporation) | |
| (15) Methyl paraben | 0.1 |
| (16) Edetate | 0.05 |
| (17) Phenoxy ethanol | 0.3 |
| (18) Ethanol | 9.0 |
| (19) Purified water | Balance |
| B. Oil phase part | |
| (20) Isododecane | 1.0 |
| (21) Liquid paraffin | 1.0 |
| (22) Isodecyl neopentanoate (IOB = 0.2) | 5.0 |
| (23) Decamethylcyclopentasiloxane | 1.0 |
| (24) Perfume | Q.S. |
| C. Neutralizer | |
| (25) Potassium hydroxide | Q.S. |

(Production Method)

At room temperature, (1) mixed with (18) and (19) was homogeneously stirred with a homomixer to prepare vesicle particles, and then the other aqueous phase components were added thereto. The mixture was stirred sufficiently to obtain Phase A (aqueous phase part). Phase A was mixed with Phase B (oil phase part), which had been prepared in advance, and the mixture was treatment with a homomixer to homogenize emulsion particles. Then, the neutralizer (25) was added thereto.

All of the oil-in-water cosmetics of Formulation Examples 8 to 10 were excellent in usability (spreadability, finish on skin, and non-stickiness) and emulsion stability.

Formulation Example 11

Essence

| | |
|---|---|
| (1) Polyoxyethylene (10) hydrogenated castor oil | 2.0 |
| (2) Dimethicone | 3.0 |
| (3) Pentaerythritol tetra(behenate/benzoate/ethylhexanoate) | 3.0 |
| (4) Pentaerythritol tetra-2-ethylhexanoate | 2.0 |
| (5) Squalane | 2.0 |
| (6) Carboxyvinyl polymer | 0.2 |
| (7) Potassium hydroxide | Q.S. |
| (8) Dipropylene glycol | 5.0 |
| (9) Glycerin | 5.0 |
| (10) Sodium hyaluronnate | 0.001 |
| (11) Dipotassium glycyrrhizinate | 0.1 |
| (12) Xanthan gum | 0.1 |
| (13) Phenoxy ethanol | Q.S. |
| (14) Tocopherol acetate | 0.1 |
| (15) Perfume | Q.S. |
| (16) Purified water | Balance |
| (17) Ethanol | 7.0 |

(Production Method)

(1), (16), and (17) were mixed and stirred with a homo-mixer. (2) to (5) and (14) to (15) heated to 70° C. were added thereto while stirred with a homomixer to be emulsified. (6) and (8) to (13) were added to the emulsion, which was then neutralized with (7).

Formulation Example 12

Oil-In-Water Sunscreen Milky Lotion

| | |
|---|---|
| (1) Polyoxyethylene (10) hydrogenated castor oil | 3.0 |
| (2) Dimethicone | 1.0 |
| (3) Glyceryl diisostearate | 3.0 |
| (4) Octocrylene | 5.0 |
| (5) Octyl methoxycinnamate | 5.0 |
| (6) t-Butyl methoxydibenzoylmethane | 2.0 |
| (7) Diethylhexyl succinate | 2.0 |
| (8) Succinoglycan | 0.3 |
| (9) Tranexamic acid | 1.0 |
| (10) Dipropylene glycol | 5.0 |
| (11) Trisodium edetate | 0.1 |
| (12) Phenoxy ethanol | 0.5 |
| (13) Perfume | Q.S. |
| (14) Purified water | Balance |
| (15) Ethanol | 7.0 |

(Production Method)

(1), (14), and (15) were mixed and stirred with a homo-mixer. (2) to (7) and (13) heated to 70° C. were added thereto while stirred with a homomixer to be emulsified. (8) to (12) were added to and mixed with the emulsion.

Formulation Example 13

Oil-In-Water Emulsion Foundation

| | |
|---|---|
| (1) Polyoxyethylene (20) hydrogenated castor oil | 2.0 |
| (2) 1,3-Butylene glycol | 5.0 |
| (3) Glycerin | 3.0 |

-continued

| | |
|---|---|
| (4) Dimethylpolysiloxane | 2.0 |
| (5) Di(phytosteryl/2-octyldodecyl) N-lauroyl-L-glutamate | 2.0 |
| (6) Tripropylene glycol dineopentanoate | 6.0 |
| (7) Cetyl 2-ethylhexanoate | 2.0 |
| (8) DL-α-tocopherol acetate | 0.1 |
| (9) Titanium oxide | 4.0 |
| (10) Kaolin | 3.0 |
| (11) Silicic anhydride | 2.0 |
| (12) Red iron oxide | Q.S. |
| (13) Yellow iron oxide | Q.S. |
| (14) Black iron oxide | Q.S. |
| (15) Xanthan gum | 0.3 |
| (16) Methyl paraben | 0.2 |
| (17) Perfume | Q.S. |
| (18) Purified water | Balance |
| (19) Ethanol | 7.0 |

(Production Method)

(1), (18), and (19) were mixed and stirred with a homo-mixer. (2) to (8) and (17) heated to 70° C. were added thereto while stirred with a homomixer to be emulsified. (9) to (16) were added to and mixed with the emulsion.

All of the oil-in-water cosmetics of Formulation Examples 11 to 13 provided a light fresh feeling in use without stickiness (stickiness is peculiar to an oil-in-water emulsified cosmetic containing a highly-polar oil), and were also excellent in emulsion stability.

What is claimed is:

1. An oil-in-water cosmetic comprising:
(a) oil-droplet particles consisting of an oil component to be emulsified;
(b) vesicle particles for stabilizing the oil-droplet particles; and
(c) an aqueous phase containing water and ethanol,
wherein the vesicle particles adhere to surfaces of the oil-droplet particles as an independent emulsifying and dispersing agent phase such that outer surfaces of the vesicle particles are in contact with the surfaces of the oil-droplet particles, and
the vesicle particles are formed of an amphiphilic substance being a polyoxyethylene hydrogenated castor oil derivative represented by formula (I):

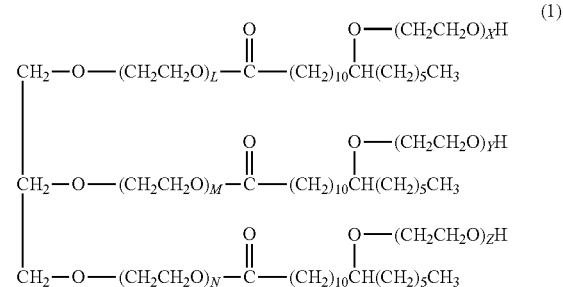

wherein E=L+M+N+X+Y+Z, and said E which represents the average addition mole number of ethylene oxide is 10 to 20,
wherein a production method of the oil-in-water cosmetic comprises:
mixing the aqueous phase comprising water and ethanol with the amphiphilic substance which spontaneously forms vesicles to prepare a vesicle dispersion in which vesicle particles are formed in the aqueous phase; and
mixing the oil component to be emulsified with the vesicle dispersion to obtain the oil-in-water cosmetic.

2. The oil-in-water cosmetic according to claim 1, wherein the amphiphilic substance spontaneously forms vesicle particles, and the vesicle particles are localized on surfaces of the oil-droplet particles.

3. The oil-in-water cosmetic according to claim 1, wherein the ethanol contained therein is 5 to 50% by mass with respect to total amount of cosmetic.

4. The oil-in-water cosmetic according to claim 1 further comprising an UV absorber.

5. The oil-in-water cosmetic according to claim 4, wherein the UV absorber is one or more selected from octocrylene, octyl methoxycinnamate, 4-tert-butyl-4'-methoxybenzoyl-methane, methylene bis-benzotriazolyl tetramethylbutylphenol, bis-ethylhexyloxyphenol methoxyphenyl triazine, diethylamino hydroxybenzoyl hexyl benzoate, ethylhexyl triazone, phenylbenzimidazole sulfonic acid, dimethicone diethylbenzalmalonate, diethylhexyl butamido triazone, and 2-(4-(2-ethylhexyloxy)-2-hydroxyphenyl)-2H-benzotriazol.

6. The oil-in-water cosmetic according to claim 1, further comprising one or more selected from carboxyvinyl polymer, succinoglycan, agar, hydroxyethyl cellulose, hydroxypropyl cellulose, and xanthan gum.

7. A production method of an oil-in-water cosmetic, comprising:
mixing an aqueous phase comprising water and ethanol with an amphiphilic substance which spontaneously forms vesicles to prepare a vesicle dispersion in which vesicle particles are formed in the aqueous phase, the amphiphilic substance being a polyoxyethylene hydrogenated castor oil derivative represented by formula (1):

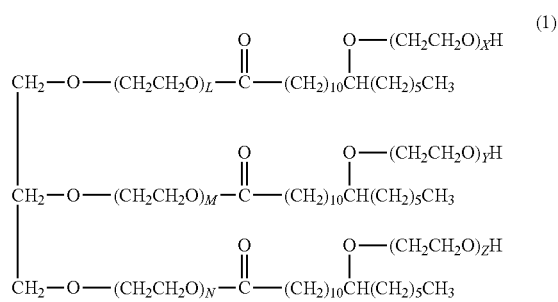

wherein E=L+M+N+X+Y+Z, and said E which represents the average addition mole number of ethylene oxide is 10 to 20; and mixing an oil component to be emulsified with the vesicle dispersion to obtain the oil-in-water cosmetic.

8. The oil-in-water cosmetic according to claim 2, wherein the ethanol contained therein is 5 to 50% by mass with respect to total amount of cosmetic.

9. The oil-in-water cosmetic according to claim 2, further comprising an UV absorber.

10. The oil-in-water cosmetic according to claim 2, further comprising one or more selected from carboxyvinyl polymer, succinoglycan, agar, hydroxyethyl cellulose, hydroxypropyl cellulose, and xanthan gum.

* * * * *

UNITED STATES PATENT AND TRADEMARK OFFICE
CERTIFICATE OF CORRECTION

PATENT NO. : 8,926,996 B2
APPLICATION NO. : 13/132112
DATED : January 6, 2015
INVENTOR(S) : Masanori Yoshimura et al.

It is certified that error appears in the above-identified patent and that said Letters Patent is hereby corrected as shown below:

In the Claims

Column 26, Lines 42 to 56, (Claim 1), delete

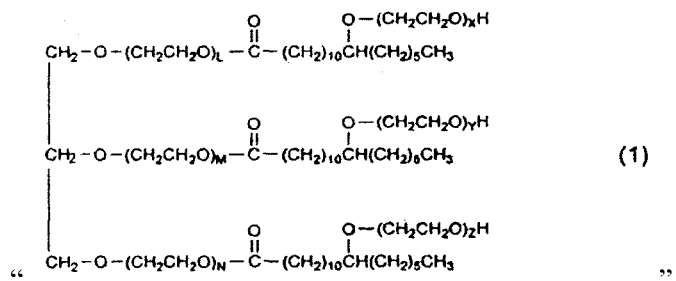

and insert

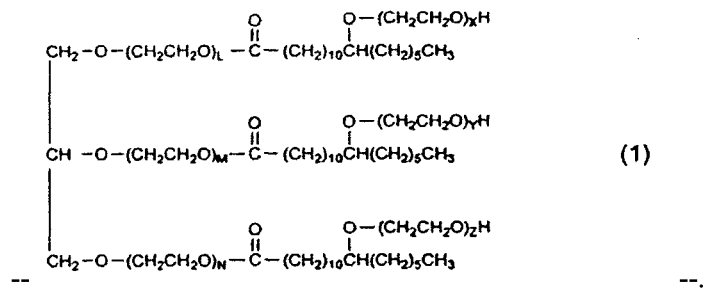

Column 28, Lines 1 to 14, (Claim 7), delete

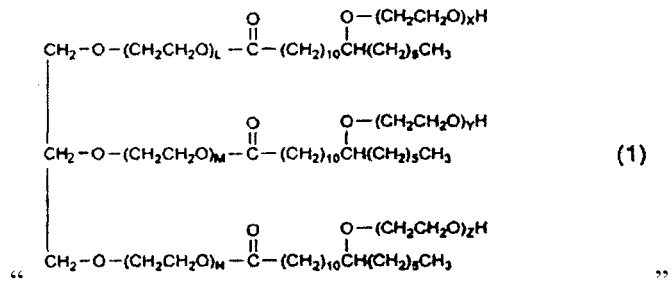

Signed and Sealed this
Fourth Day of August, 2015

Michelle K. Lee
*Director of the United States Patent and Trademark Office*

CERTIFICATE OF CORRECTION (continued)
U.S. Pat. No. 8,926,996 B2 and insert

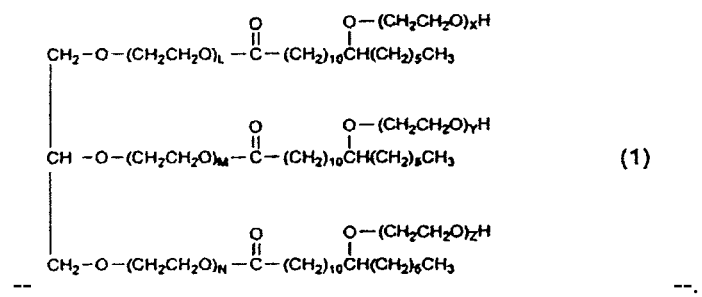

(1)

--.